United States Patent
Zhang et al.

(10) Patent No.: US 9,773,326 B2
(45) Date of Patent: Sep. 26, 2017

(54) METHOD AND DEVICE FOR CALIBRATING COMPUTERIZED TOMOGRAPHY (CT) IMAGE AND CT SYSTEM INCLUDING THE SAME

(71) Applicants: TSINGHUA UNIVERSITY, Beijing (CN); NUCTECH COMPANY LIMITED, Beijing (CN)

(72) Inventors: Li Zhang, Beijing (CN); Xin Jin, Beijing (CN); Qingping Huang, Beijing (CN); Yunda Sun, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 33 days.

(21) Appl. No.: 14/751,044

(22) Filed: Jun. 25, 2015

(65) Prior Publication Data
US 2015/0379745 A1 Dec. 31, 2015

(30) Foreign Application Priority Data

Jun. 25, 2014 (CN) .......................... 2014 1 0295062

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/5205* (2013.01); *A61B 6/583* (2013.01);
(Continued)

(58) Field of Classification Search
None
See application file for complete search history.

(56) References Cited

U.S. PATENT DOCUMENTS 6,801,594 B1 * 10/2004 Ali .......................... A61B 6/032
378/114
8,712,679 B1 * 4/2014 Mostofi .................. G09B 29/00
340/552
(Continued)

FOREIGN PATENT DOCUMENTS

CN 101266216 A 9/2008
CN 103226113 A 7/2013
(Continued)

*Primary Examiner* — Tahmina Ansari
(74) *Attorney, Agent, or Firm* — McDermott Will & Emery LLP (57) ABSTRACT

The present invention provides a CT image calibration method and device and a CT system. The method includes: arranging a fixed calibration element at the outside of a channel area and within the maximal reconstruction area of a CT scanning device, and storing the theoretical value of the fixed calibration element; collecting the projection data of the fixed calibration element to obtain the actual reconstructed image of the fixed calibration element; and comparing the actual reconstructed image with the stored corresponding theoretical value, to establish a mapping function for correcting the actual reconstructed image into the theoretical value. By adopting the present invention, the calibration quality can be effectively improved, the image calibration effect is enhanced, the reliability of the CT scanning device is improved and the maintenance cost is saved, thus the practical application value is very high.

15 Claims, 3 Drawing Sheets

(51) Int. Cl.
*G01N 23/04* (2006.01)
*G01V 5/00* (2006.01)
*A61B 6/03* (2006.01)
*A61B 6/00* (2006.01)

(52) U.S. Cl.
CPC .......... *G01N 23/046* (2013.01); *G01V 5/005* (2013.01); *G01V 5/0041* (2013.01); *G06T 2207/10081* (2013.01)

(56) References Cited

U.S. PATENT DOCUMENTS

| | | | |
|---|---|---|---|
| 9,011,217 B2* | 4/2015 | Raible | B64D 13/00 454/71 |
| 2005/0046436 A1* | 3/2005 | Frankowsky | G01R 31/3191 324/750.02 |
| 2007/0290125 A1* | 12/2007 | Wang | G01T 1/1648 250/252.1 |
| 2008/0101532 A1* | 5/2008 | Tkaczyk | A61B 6/541 378/8 |
| 2009/0139768 A1* | 6/2009 | Castillo | E21B 25/10 175/50 |
| 2010/0099347 A1* | 4/2010 | Raible | B64D 13/00 454/76 |
| 2013/0189188 A1* | 7/2013 | Gulsen | A61B 5/0071 424/9.6 |
| 2015/0379745 A1* | 12/2015 | Zhang | G01N 23/046 382/131 |

FOREIGN PATENT DOCUMENTS

| | | |
|---|---|---|
| CN | 103326143 A | 9/2013 |
| CN | 104091329 A | 10/2014 |
| WO | WO-2013/185011 A1 | 12/2013 |

* cited by examiner

METHOD AND DEVICE FOR CALIBRATING COMPUTERIZED TOMOGRAPHY (CT) IMAGE AND CT SYSTEM INCLUDING THE SAME

TECHNICAL FIELD

The present invention relates to the technical field of radiation imaging detection, and particularly relates to a CT image calibration method and device and a CT system.

BACKGROUND

Since CT technology can eliminate the influence of overlapped objects, it plays an important role in such occasions as security check and the like. In traditional CT, projection data on different angles are obtained by rotation of an X ray source and a detector by using a slip ring device, and a tomographic image is obtained by a reconstruction method, so as to obtain the internal information of a detected luggage. Multi-energy spectrum analysis refers to distinguishing a certain material by means of the difference of the material on absorption properties of X rays with different energy. The CT technology is cooperated with the multi-energy spectrum analysis technology to cause the existing luggage inspection equipment to reconstruct the atomic number and electron density at any position in a detected matter, in order to identify the type of the matter and play a good effect in the detection of explosives, narcotics, etc.

However, no matter the traditional CT or the multi-spectrum CT, due to the inconsistency of the X-Ray tube and the detector, reconstructed images of CT equipment with the same model always have biases on pixel values, with the increase of running hours and the ageing of the tube and the detector, even if for the same CT equipment, the reconstructed images will also drift on values and deviate from the conditions when the equipment is out of a factory. In order to solve the problems above, when the CT equipment is out of the factory and periodically maintained, calibration work will be carried out by scanning a workpiece made from a particular material, and comparing a numerical value of a reconstructed image with a true value of the workpiece to determine a post-calibrated parameter, so as to achieve a post-calibration of a CT image.

However, the above post-calibration method has the following disadvantages: on one hand, the ageing of the CT equipment is an ongoing process, while the calibration process can only be carried out periodically, for example, 1-2 times every year, which means that the post-calibrated parameter cannot be the optimal within all times, moreover, since the calibration process has strong technicality and must be achieved by a maintenance engineer, the maintenance cost is increased, and the normal working hours of the equipment may be occupied; on the other hand, due to the influence from the detector, conveyer belt, channel shape, reconstruction algorithm and the like, the difference between the pixel values and the ideal value is not the same in different areas of the CT image, while the traditional calibration method is done by placing a mid- or small-sized tool box containing the calibration workpiece on a CT conveyer belt to issue a calibration scan, thus in this method, only the image values near the conveyer belt is accurate, while an optimal correction effect cannot be achieved in other areas of the image.

SUMMARY

(1) Technical Problems to be Solved

The present invention provides a CT image calibration method and device and a CT system, so as to solve the technical problems of non-timely calibration and low accuracy in post-calibration technology of CT images in the prior art.

(2) Technical Solutions

To solve the technical problems above, the present invention provides a CT image calibration method, including:
arranging a fixed calibration element at the outside of a channel area and within the maximal reconstruction area of a CT scanning device, and storing the theoretical value of the fixed calibration element;
collecting the projection data of the fixed calibration element to obtain the actual reconstructed image of the fixed calibration element; and
comparing the actual reconstructed image with the stored corresponding theoretical value, to establish a mapping function for correcting the actual reconstructed image into the theoretical value.

Further, one or more groups of fixed calibration elements are arranged, and one or more fixed calibration elements are arranged in each group.

Further, when one group including multiple fixed calibration elements is arranged, the step 103 further comprises:
using the multiple fixed calibration elements in the group as mutual references, establishing a mapping relationship of the actual reconstructed image and the theoretical value in one or more of linear, polynomial and exponential forms, and establishing the mapping function for correcting the actual reconstructed image into the theoretical value according to the mapping relationship.

Further, when multiple groups of fixed calibration elements are arranged, the step 103 further comprises:
establishing a mapping relationship of the actual reconstructed image and the theoretical value in the same group in one or more of linear, polynomial and exponential forms, and establishing a local mapping function for correcting the actual reconstructed image into the theoretical value according to the mapping relationship; and
obtaining a global mapping function of the whole reconstruction area using a linear and/or polynomial interpolation method, according to the local mapping functions of each group and the spatial position relationship of the groups.

Further, the actual reconstructed image of the fixed calibration element comprises one or more reconstructed images of high energy attenuation coefficient, low energy attenuation coefficient, attenuation coefficient under particular X ray energy, atomic number, electron density, and density distribution with a particular element as a base material; and accordingly, the theoretical value of the fixed calibration element comprises one or more theoretical values of high energy attenuation coefficient, low energy attenuation coefficient, attenuation coefficient under particular X ray energy, atomic number, electron density, and density distribution with a particular element as a base material.

Further, the method further includes:
collecting projection data and performing image reconstruction on a scanning object in the channel area of the CT scanning device, to obtain the scanning reconstructed image of the scanning object; and correcting the scanning reconstructed image by using the mapping function to obtain a corrected reconstructed image.

In another aspect, the present invention further provides a CT image calibration device, including: a fixed calibration element, a storage unit, a collection unit and a mapping unit, wherein:

the fixed calibration element is arranged at the outside of a channel area and within the maximal reconstruction area of a CT scanning device;

the storage unit is used for storing the theoretical value of the fixed calibration element;

the collection unit is used for collecting the projection data of the fixed calibration element to obtain the actual reconstructed image of the fixed calibration element; and the mapping unit is used for comparing the actual reconstructed image with the stored corresponding theoretical value, to establish a mapping function for correcting the actual reconstructed image into the theoretical value.

Further, one or more groups of the fixed calibration elements are arranged, and one or more fixed calibration elements are arranged in each group.

Further, the mapping unit is further used for:

when one group comprising multiple fixed calibration elements is arranged, using the multiple fixed calibration elements in the group as mutual references, establishing a mapping relationship of the actual reconstructed image and the theoretical value in one or more of linear, polynomial and exponential forms, and then establishing the mapping function for correcting the actual reconstructed image into the theoretical value according to the mapping relationship.

Further, the mapping unit is further used for:

when multiple groups of the fixed calibration elements are arranged, establishing a mapping relationship of the actual reconstructed image and the theoretical value in the same group in one or more of linear, polynomial and exponential forms, and establishing a local mapping function for correcting the actual reconstructed image into the theoretical value according to the mapping relationship; and obtaining a global mapping function of the whole reconstruction area using a linear and/or polynomial interpolation method, according to the local mapping function of each group and the spatial position relationship of the groups.

Further, the actual reconstructed image of the fixed calibration element comprises one or more reconstructed images of high energy attenuation coefficient, low energy attenuation coefficient, attenuation coefficient under particular X ray energy, atomic number, electron density, and density distribution with a particular element as a base material; and accordingly, the theoretical value of the fixed calibration element comprises one or more theoretical values of high energy attenuation coefficient, low energy attenuation coefficient, attenuation coefficient under particular X ray energy, atomic number, electron density, and density distribution with a particular element as a base material.

Further, the material of the fixed calibration element is: one or more of water, graphite and aluminum.

Further, the fixed calibration element is arranged at one or more positions of the channel side face, the channel top and the lower side of the conveyer belt of the CT scanning device.

Further, the collection unit is further used for collecting projection data and performing image reconstruction on a scanning object in the channel area of the CT scanning device, to obtain the scanning reconstructed image of the scanning object; and the device further includes a correction unit respectively connected with the collection unit and the mapping unit and used for correcting the scanning reconstructed image by using the mapping function to obtain a corrected reconstructed image.

In a third aspect, the present invention further provides a CT system, which includes any one of the above-mentioned CT image calibration devices.

(3) Beneficial Effects

Therefore, in the CT image calibration method and device and the CT system provided by the present invention, the fixed calibration element can be used for calibrating the CT scanning device in real time, and the periodical manual post-calibration procedure in the traditional calibration method of the CT scanning device is omitted, thereby effectively improving the calibration quality, enhancing the image calibration effect, improving the reliability of the CT scanning device, saving the maintenance cost and obtaining a very high practical application value; moreover, the calibration method provided by the present invention may be used for obtaining the corrected values of different parts within the maximal reconstruction area of the CT scanning device without being merely limited to the neighborhood of the channel area, thus more precise image correction may be achieved.

BRIEF DESCRIPTION OF THE DRAWINGS

To illustrate technical solutions in the embodiments of the present invention or in the prior art more clearly, a brief introduction on the accompanying drawings which are needed in the description of the embodiments or the prior art is given below. Apparently, the accompanying drawings in the description below are merely some of the embodiments of the present invention, based on which other drawings may be obtained by those of ordinary skill in the art without any creative effort.

DETAILED DESCRIPTION OF THE PREFERRED EMBODIMENTS

In order to make the purposes, technical solutions and advantages of the embodiments of the present invention clearer, a clear and complete description of the technical solutions in the embodiments of the present invention will be given below in combination with accompanying drawings in the embodiments of the present invention. Apparently, the embodiments described below are merely a part, but not all of the embodiments of the present invention. All of other embodiments obtained by those of ordinary skill in the art based on the embodiments of the present invention without any creative effort fall into the protection scope of the present invention.

Figure 1:
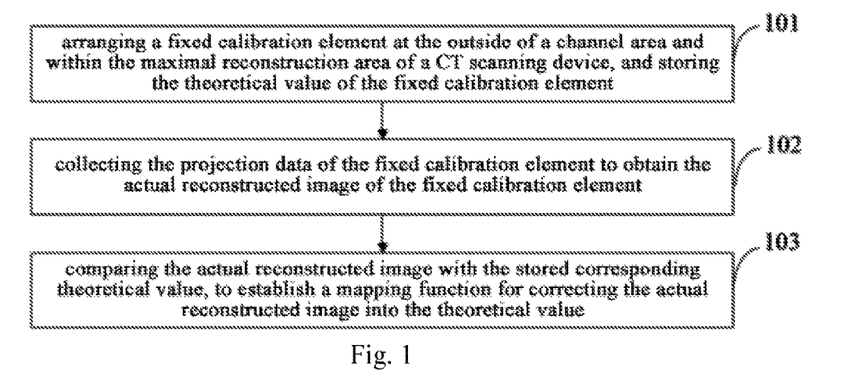
FIG. 1 is a basic flowchart of a CT image calibration method in an embodiment of the present invention.

The embodiment of the present invention firstly provides a CT image calibration method, refer to FIG. 1, including:

step 101: arranging a fixed calibration element at the outside of a channel area and within the maximal reconstruction area of a CT scanning device, and storing the theoretical value of the fixed calibration element;

step 102: collecting the projection data of the fixed calibration element to obtain the actual reconstructed image of the fixed calibration element; and step 103: comparing the actual reconstructed image with the stored corresponding theoretical value, to establish a mapping function for correcting the actual reconstructed image into the theoretical value.

Therefore, in the CT image calibration method provided by the embodiment of the present invention, the fixed calibration element can be used for calibrating the CT scanning device in real time, and the periodical manual post-calibration procedure in the traditional calibration method of the CT scanning device is omitted, thereby effectively improving the calibration quality, enhancing the image calibration effect, improving the reliability of the CT scanning device, saving the maintenance cost and obtaining a very high practical application value.

Preferably, one or more groups of the fixed calibration elements may be arranged, and one or more fixed calibration elements may be arranged in each group, which depends on the type of a reconstructed image to be measured.

Preferably, when one group including multiple fixed calibration elements is arranged, the actual reconstructed image may be processed in the following manner: using the multiple fixed calibration elements in the group as mutual references, establishing a mapping relationship of the actual reconstructed image and the theoretical value in one or more of linear, polynomial and exponential forms, and then establishing the mapping function for correcting the actual reconstructed image into the theoretical value according to the mapping relationship.

Preferably, when multiple groups of the fixed calibration elements are arranged, the fixed calibration elements may be firstly grouped and then are integrated by considering the spatial position relationship of the groups, and specifically may include:

establishing a mapping relationship of the actual reconstructed image and the theoretical value in the same group in one or more of linear, polynomial and exponential forms, and establishing a local mapping function for correcting the actual reconstructed image into the theoretical value according to the mapping relationship; and obtaining a global mapping function of the whole reconstruction area using a linear and/or polynomial interpolation method, according to the local mapping function of each group and the spatial position relationship of the groups.

The method provided by the embodiment of the present invention may be used for calibrating a variety of CT reconstructed images, specifically including such data as high energy attenuation coefficient, low energy attenuation coefficient, attenuation coefficient under particular X ray energy, atomic number, electron density and density distribution with a particular element as a base material of the fixed calibration element, and the particular element herein may be such elements as carbon, water or aluminum or the like.

Preferably, scanning reconstructed image correction may be performed on the CT scanning device according to the calibration method in the embodiment of the present invention, and specifically, the method may further include:

collecting projection data and performing image reconstruction on a scanning object in the channel area of the CT scanning device, to obtain the scanning reconstructed image of the scanning object; and correcting the scanning reconstructed image by using the mapping function to obtain a corrected reconstructed image.

Figure 2:
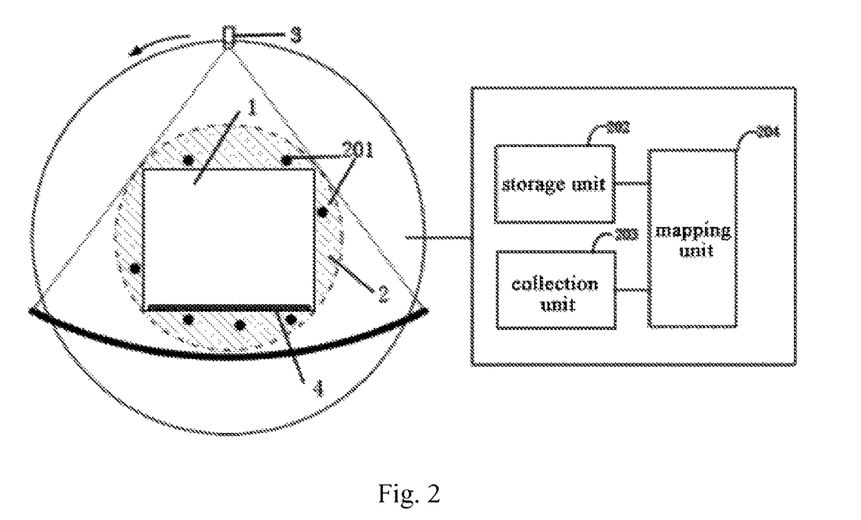
FIG. 2 is a schematic diagram of a basic structure of a CT image calibration device in an embodiment of the present invention.

The embodiment of the present invention further provides a CT image calibration device, refer to FIG. 2, including:

a fixed calibration element 201 arranged at the outside of a channel area 1 and within the maximal reconstruction area 2 of a CT scanning device;

a storage unit 202 used for storing the theoretical value of the fixed calibration element 201;

a collection unit 203 used for collecting the projection data of the fixed calibration element 201 to obtain the actual reconstructed image of the fixed calibration element 201; and a mapping unit 204 used for comparing the actual reconstructed image with the stored corresponding theoretical value, to establish a mapping function for correcting the actual reconstructed image into the theoretical value.

In FIG. 2, numeral 3 represents a ray source and numeral 4 represents a conveying belt.

Preferably, one or more groups of fixed calibration elements 201 may be arranged, and one or more fixed calibration elements may also be arranged in each group.

Preferably, the mapping unit 204 may also be used for: when one group including multiple fixed calibration elements 201 is arranged, using the multiple fixed calibration elements 201 in the group as mutual references, establishing a mapping relationship of the actual reconstructed image and the theoretical value in one or more of linear, polynomial and exponential forms, and then establishing the mapping function for correcting the actual reconstructed image into the theoretical value according to the mapping relationship.

Preferably, the mapping unit 204 may be further used for: when multiple groups of the fixed calibration elements 201 are arranged, establishing a mapping relationship of the actual reconstructed image and the theoretical value in the same group in one or more of linear, polynomial and exponential forms, and establishing a local mapping function for correcting the actual reconstructed image into the theoretical value according to the mapping relationship; and obtaining a global mapping function of the whole reconstruction area 2 using a linear and/or polynomial interpolation method, according to the local mapping function of each group and the spatial position relationship of the groups.

Preferably, the actual reconstructed image of the fixed calibration element 201 may include one or more reconstructed images of high energy attenuation coefficient, low energy attenuation coefficient, attenuation coefficient under particular X ray energy, atomic number, electron density and density distribution with a particular element as a base material of the fixed calibration element 201; accordingly, the theoretical value of the fixed calibration element 201 may also include one or more theoretical values of high energy attenuation coefficient, low energy attenuation coefficient, attenuation coefficient under particular X ray energy, atomic number, electron density and density distribution with a particular element as a base material of the fixed calibration element 201, and the particular element herein may be such elements as carbon, water or aluminum or the like.

Preferably, the material of the fixed calibration element 201 may be such calibration materials as water, graphite, aluminum, etc.

Preferably, the position of the fixed calibration element 201 may be the channel side face, the channel top and the lower side of the conveyer belt of the CT scanning device, and the like, and the corrected values of different parts within the maximal reconstruction area 2 of the CT scanning device can be obtained without being merely limited to the neighborhood of the channel area 1, thus more precise image correction can be achieved.

Preferably, the collection unit 203 may be further used for collecting projection data and performing image reconstruction on a scanning object in the channel area 1 of the CT scanning device, to obtain the scanning reconstructed image of the scanning object; and accordingly, the device may also include a correction unit respectively connected with the collection unit 203 and the mapping unit 204 and used for correcting the scanning reconstructed image by using the mapping function to obtain a corrected reconstructed image.

Figure 3:
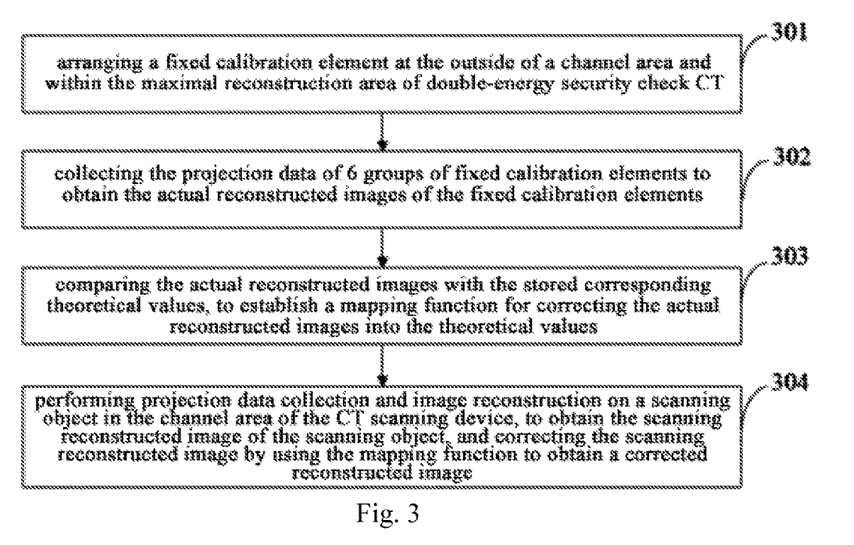
FIG. 3 is a practical application flowchart of a CT image calibration device in an embodiment of the present invention.

The specific implementation process of the embodiment of the present invention will be described below in detail with the practical application flow of the CT image calibration device in the embodiment of the present invention in double-energy security check CT as an example, refer to FIG. 3:

step 301: arranging a fixed calibration element at the outside of a channel area and within the maximal reconstruction area of double-energy security check CT.

Figure 4:
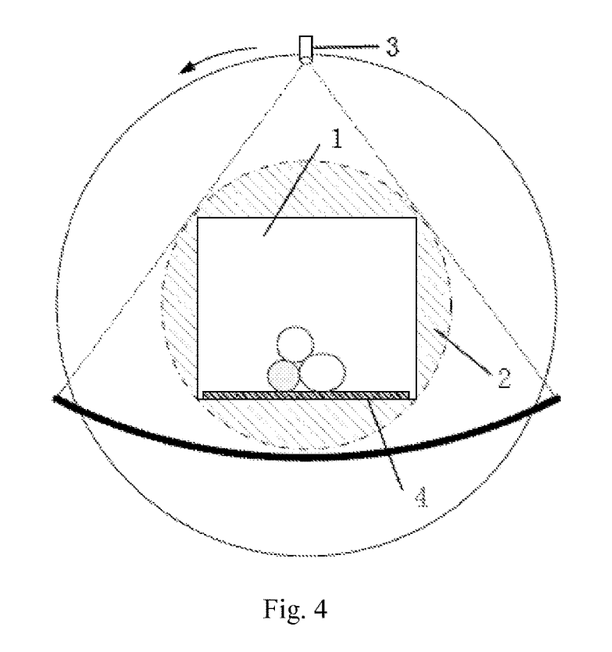
FIG. 4 is a schematic diagram of the channel area and the maximal reconstruction area of a CT scanning device.

In general, the effective area of a scanning channel when an object may be placed is smaller than the theoretically maximal reconstruction area of the scanning device, as shown in FIG. 4, thus a part of areas out of the channel may be reconstructed, but in actual work, no object is possibly located at the outside of the channel, thus the part is not reconstructed in general.

Figure 5:
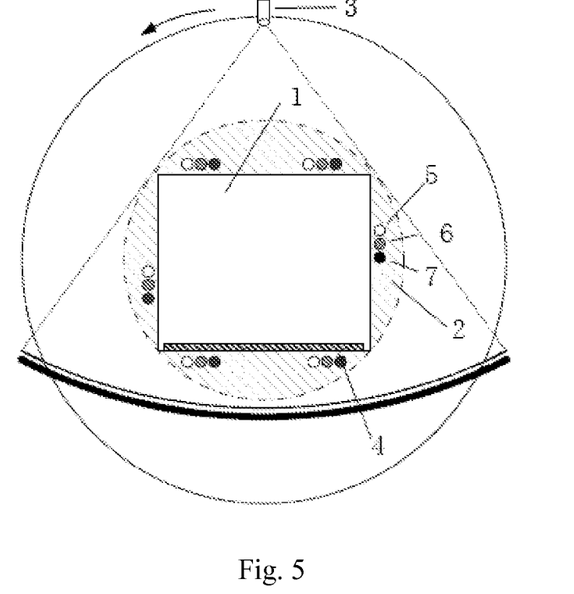
FIG. 5 is a schematic diagram of the positions of a fixed calibration element in a CT image calibration device in an embodiment of the present invention.

In the embodiment of the present invention, the area above can be utilized, the fixed calibration element is arranged at the outside of the channel area and within the maximal reconstruction area of the double-energy security check CT, wherein 6 groups of fixed calibration elements are used in total in the embodiment, each group of the fixed calibration elements includes a pure water column 5, a graphite column 6 and an aluminum column 7, refer to FIG. 5, and various theoretical values of the above-mentioned fixed calibration elements are stored. In the double-energy security check CT, four reconstructed images of high energy attenuation coefficient, low energy attenuation coefficient, attenuation coefficient under particular X ray energy, atomic number and electron density may be reconstructed by means of the double-energy CT reconstruction principle, since the reconstructed images of the atomic number and the electron density play an important role of identifying the materials, in the embodiment, the reconstructed images of the atomic number and the electron density are selected for calibration. The theoretical values of the atomic number and the electron density of the above-mentioned three materials are known, and in the embodiment, the theoretical values of the atomic number and the electron density of the water, graphite and aluminum materials may be stored by a storage unit.

Step 302: collecting the projection data of 6 groups of the fixed calibration elements to obtain the actual reconstructed images of the fixed calibration elements.

In the embodiment, the projection data of the above-mentioned 6 groups of the fixed calibration elements of different materials are collected by a collection unit to obtain the actual reconstructed images thereof.

Step 303: comparing the actual reconstructed images with the stored corresponding theoretical values, to establish a mapping function for correcting the actual reconstructed images into the theoretical values.

In the step, the actual reconstructed images collected by the collection unit are respectively compared with the corresponding theoretical values of the water, graphite and aluminum materials stored by the storage unit through a mapping unit, specifically:

firstly, using the multiple fixed calibration elements in the same group as mutual references, and establishing a polynomial mapping relationship of the actual reconstructed images and the corresponding theoretical values to obtain the local mapping function of each group; and then, establishing the mapping functions of various positions within the entire reconstruction range by means of the local mapping functions of 6 different positions by using a linear interpolation method.

Figure 6:
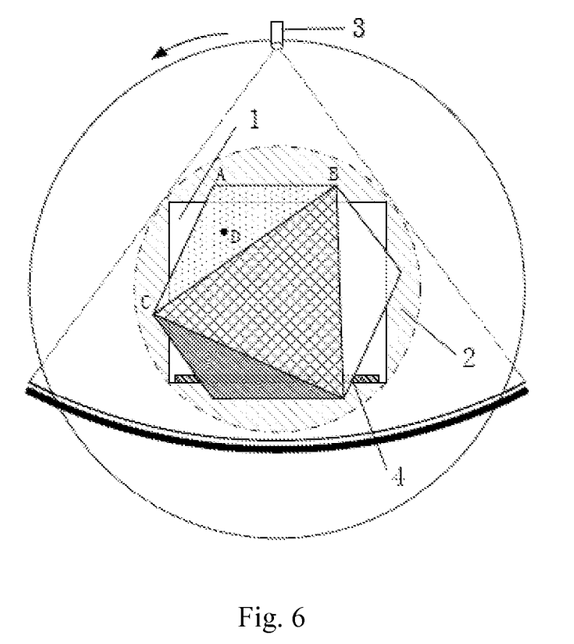
FIG. 6 is a schematic diagram of a method for calibrating linear interpolations in a CT image calibration device in an embodiment of the present invention.

Or, the mapping functions of various positions within the entire reconstruction range are directly established according to the spatial positions of 6 groups of the fixed calibration elements with different positions. FIG. 6 shows a realization means of linear interpolation by means of a method of establishing a triangle, for any determined position D, a minimal triangle containing a point D is found firstly, the triangle is composed of three points A, B, C, then the actual reconstructed images of three material blocks of the point D are estimated by means of the actual reconstructed images of three material blocks of the three points A, B, C. This process may be achieved by bilinear interpolation, and then the mapping function of the point D is obtained according to the deduced actual reconstructed images of the three materials of the point D, in order to respectively correct the atomic number and the electron density of the point D.

Step 304: collecting projection data and performing image reconstruction on a scanning object in the channel area of the CT scanning device, to obtain the scanning reconstructed image of the scanning object; and correcting the scanning reconstructed image by using the mapping function to obtain a corrected reconstructed image.

In the step, firstly the collection unit is used for collecting the projection data and performing the image reconstruction on the scanning object in the channel area of the CT scanning device, to obtain the scanning reconstructed image of the scanning object, then, the scanning reconstructed image is corrected according to the primarily established mapping function, and the scanning reconstructed image is mapped back to the theoretical value to obtain the corrected reconstructed image.

So far, the entire process of the practical application flow of the CT image calibration device in the embodiment of the present invention is completed.

The storage unit, the collection unit, the mapping unit and the correction unit in the device of the embodiment of the present invention may be located in a data collection and image reconstruction device of the CT scanning device, may also be connected with the CT scanning device, may become an integrity and may also be composed of multiple fissions, as long as the above-mentioned functional units are provided. Those skilled in the art may achieve the above-mentioned functional units by adopting hardware, software, firmware or the combination of the three.

The embodiment of the present invention further provides a CT system, which includes any above-mentioned CT image calibration device.

Therefore, the embodiment of the present invention at least has the following beneficial effects:

in the CT image calibration method and device and a CT system provided by the embodiment of the present invention, the fixed calibration element may be used for calibrating the CT scanning device in real time, and the periodical manual post-calibration procedure in the traditional calibration method of the CT scanning device is omitted, thereby effectively improving the calibration quality, enhancing the image calibration effect, improving the reliability of the CT scanning device, saving the maintenance cost and obtaining a very high practical application value; moreover, the calibration method provided by the embodiment of the present invention may be used for obtaining the corrected values of different parts within the maximal reconstruction area of the CT scanning device without being merely limited to the neighborhood of the channel area, thus more precise image correction can be achieved.

Finally, it should be noted that the above-mentioned embodiments are merely used for illustrating the technical solutions of the present invention, rather than limiting them; although the present invention has been described in detail with reference to the foregoing embodiments, those of ordinary skill in the art should understand that they could still make modifications to the technical solutions recorded in the foregoing embodiments or make equivalent substitutions to a part of the technical features; and these modifications or substitutions do not make the essence of the corresponding technical solutions depart from the spirit and scope of the technical solutions of the embodiments of the present invention.

The invention claimed is:

1. A computerized tomography (CT) image calibration method, comprising:
   arranging a fixed calibration element at the outside of a channel area and within the maximal reconstruction area of a CT scanning device, and storing a theoretical value of the fixed calibration element;
   collecting projection data of the fixed calibration element to obtain an actual reconstructed image of the fixed calibration element; and
   comparing the actual reconstructed image with the stored corresponding theoretical value, to establish a mapping function for correcting the actual reconstructed image into the theoretical value.

2. The CT image calibration method of claim 1, wherein one or more groups of the fixed calibration elements are arranged, and one or more fixed calibration elements are arranged in each of the one or more groups.

3. The CT image calibration method of claim 2, wherein when one group comprising multiple fixed calibration elements is arranged, the comparing further comprises:
   using the multiple fixed calibration elements in the group as mutual references, establishing a mapping relationship of the actual reconstructed image and the theoretical value in one or more of linear, polynomial and exponential forms, and then establishing the mapping function for correcting the actual reconstructed image into the theoretical value according to the mapping relationship.

4. The CT image calibration method of claim 2, wherein when multiple groups of fixed calibration elements are arranged, the comparing further comprises:
   establishing a mapping relationship of the actual reconstructed image and the theoretical value in the same group in one or more of linear, polynomial and exponential forms, and establishing a local mapping function for correcting the actual reconstructed image into the theoretical value according to the mapping relationship; and
   obtaining a global mapping function of the whole reconstruction area using a linear and/or polynomial interpolation method, according to the local mapping functions of each group and the spatial position relationship of the groups.

5. The CT image calibration method of claim 1, wherein
   the actual reconstructed image of the fixed calibration element comprises one or more reconstructed images of high energy attenuation coefficient, low energy attenuation coefficient, attenuation coefficient under particular X ray energy, atomic number, electron density, and density distribution with a particular element as a base material; and
   accordingly, the theoretical value of the fixed calibration element comprises one or more theoretical values of high energy attenuation coefficient, low energy attenuation coefficient, attenuation coefficient under particular X ray energy, atomic number, electron density, and density distribution with a particular element as a base material.

6. The CT image calibration method of claim 1, further comprising:
   collecting projection data and performing image reconstruction on a scanning object in the channel area of the CT scanning device, to obtain the scanning reconstructed image of the scanning object; and
   correcting the scanning reconstructed image by using the mapping function to obtain a corrected reconstructed image.

7. A computerized tomography (CT) image calibration device, comprising:
   a fixed calibration element arranged at the outside of a channel area and within the maximal reconstruction area of a CT scanning device;
   a storage device coupled to the CT scanning device and configured to store a theoretical value of the fixed calibration element;
   a collection component configured to collect projection data of the fixed calibration element to obtain an actual reconstructed image of the fixed calibration element; and
   a mapping component coupled to the storage device and the collection component and configured to compare the actual reconstructed image with the stored corresponding theoretical value, to establish a mapping function for correcting the actual reconstructed image into the theoretical value.

8. The CT image calibration device of claim 7, wherein one or more groups of fixed calibration elements are arranged, and one or more fixed calibration elements are arranged in each of the one or more groups.

9. The CT image calibration device of claim 8, wherein the mapping component is further configured to:
   when one group comprising multiple fixed calibration elements is arranged, use the multiple fixed calibration elements in the group as mutual references, establish a mapping relationship of the actual reconstructed image and the theoretical value in one or more of linear, polynomial and exponential forms, and then establish the mapping function for correcting the actual reconstructed image into the theoretical value according to the mapping relationship.

10. The CT image calibration device of claim 8, wherein the mapping component is further configured to:
   when multiple groups of the fixed calibration elements are arranged, establish a mapping relationship of the actual reconstructed image and the theoretical value in the same group in one or more of linear, polynomial and exponential forms, and establish a local mapping function for correcting the actual reconstructed image into the theoretical value according to the mapping relationship; and
   obtain a global mapping function of the whole reconstruction area using a linear and/or polynomial interpolation method, according to the local mapping function of each group and the spatial position relationship of the groups.

11. The CT image calibration device of claim 7, wherein the actual reconstructed image of the fixed calibration element comprises one or more reconstructed images of high energy attenuation coefficient, low energy attenuation coefficient, attenuation coefficient under particular X ray energy, atomic number, electron density, and density distribution with a particular element as a base material; and
   accordingly, the theoretical value of the fixed calibration element comprises one or more theoretical values of high energy attenuation coefficient, low energy attenuation coefficient, attenuation coefficient under particular X ray energy, atomic number, electron density, and density distribution with a particular element as a base material.

12. The CT image calibration device of claim 7, wherein a material of the fixed calibration element is:
   one or more of water, graphite and aluminum.

13. The CT image calibration device of claim 7, wherein the fixed calibration element is arranged at one or more positions of the channel side face, the channel top and a lower side of a conveyer belt of the CT scanning device.

14. The CT image calibration device of claim 7, wherein the collection component is further configured to collect projection data and performing image reconstruction on a scanning object in the channel area of the CT scanning device, to obtain the scanning reconstructed image of the scanning object; and
   the CT image calibration device further comprises a correction component respectively connected with the collection component and the mapping component and configured to correct the scanning reconstructed image by using the mapping function to obtain a corrected reconstructed image.

15. A computerized tomography (CT) system, comprising the CT image calibration device of claim 7.

* * * * *